United States Patent [19]
Fukunaga

[11] Patent Number: 5,815,256
[45] Date of Patent: Sep. 29, 1998

[54] APPARATUS AND METHOD FOR MEASURING IN-PLANE DISTRIBUTION OF SURFACE FREE ENERGY

[75] Inventor: Yoko Fukunaga, Yokohama, Japan

[73] Assignee: Kabushiki Kaisha Toshiba, Kawasaki, Japan

[21] Appl. No.: 797,607

[22] Filed: Feb. 7, 1997

[30] Foreign Application Priority Data

Feb. 9, 1996 [JP] Japan .................................. 8-023796

[51] Int. Cl.⁶ .................................................. G01B 11/26
[52] U.S. Cl. ........................................... 356/150; 356/138
[58] Field of Search ..................... 356/138, 150; 73/64.43, 64.52; 118/402, 425, 408–410; 427/430.1, 434.3, 434.4

[56] References Cited

U.S. PATENT DOCUMENTS

| | | |
|---|---|---|
| 4,848,270 | 7/1989 | Wakayama et al. . |
| 4,943,160 | 7/1990 | Gevelber et al. ..................... 356/138 |
| 5,286,529 | 2/1994 | Nakayama et al. . |

FOREIGN PATENT DOCUMENTS 63-32357  2/1988  Japan .

OTHER PUBLICATIONS

Chappuis et al, "Contribution to the Study of Wetting: Analysis of a Measurement Method", Journal De Chime Physique vol. 71. No. 4, 1974 Translation of entire document attached.

*Primary Examiner*—K. Hantis
*Attorney, Agent, or Firm*—Oblon, Spivak, McClelland, Maier & Neustadt, P.C.

[57] ABSTRACT

In an apparatus and method for measuring in-plane distribution of surface free energy, a target substrate is immersed in a liquid, and a parameter representing a state of meniscus to be formed at an intersection area of a target surface with a surface of the liquid is measured along the surface of the liquid. This measurement is performed by descending or ascending the substrate, thereby measuring the parameter throughout the entire surface of the target surface, and then, the in-plane distribution of the surface free energy of the target surface is calculated.

18 Claims, 12 Drawing Sheets

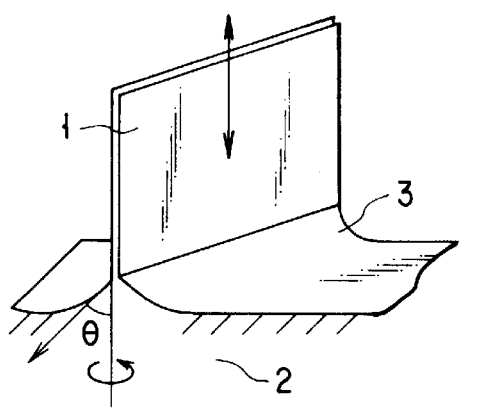
F I G. 1A
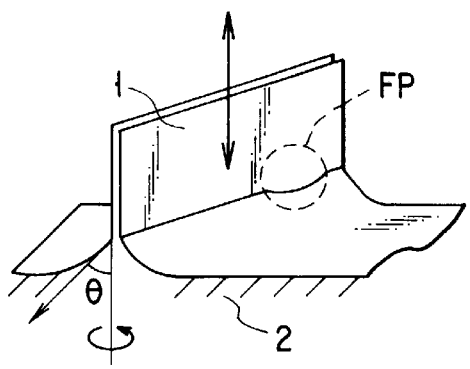
F I G. 1B
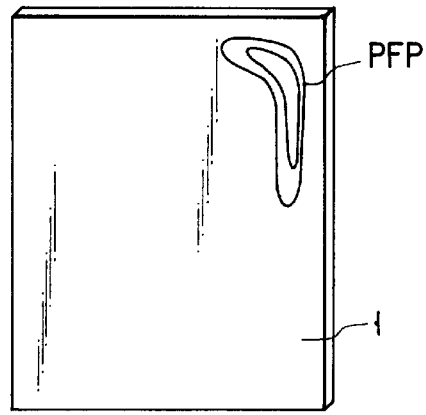
F I G. 2
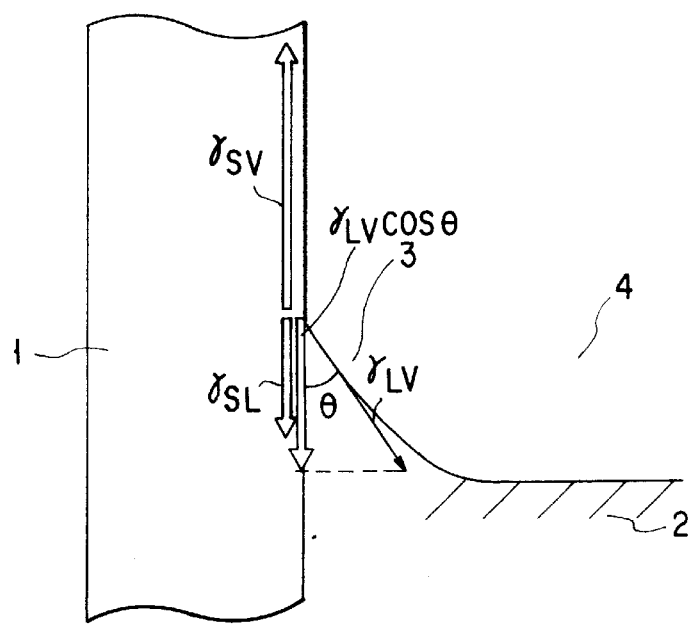
F I G. 3

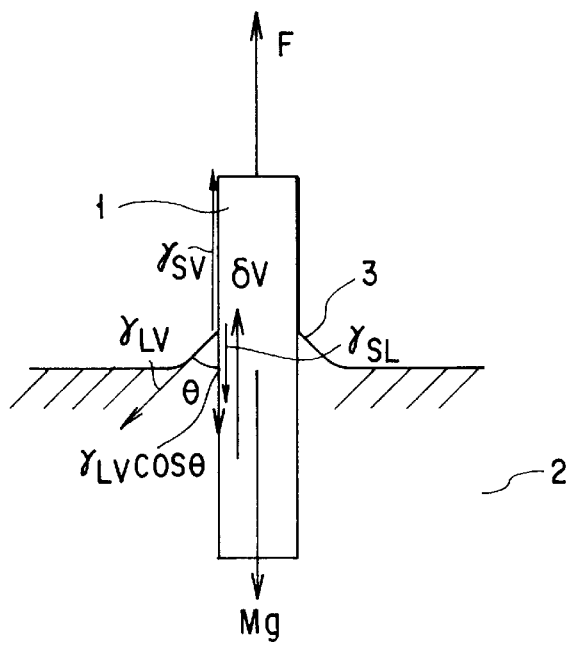
F I G. 4
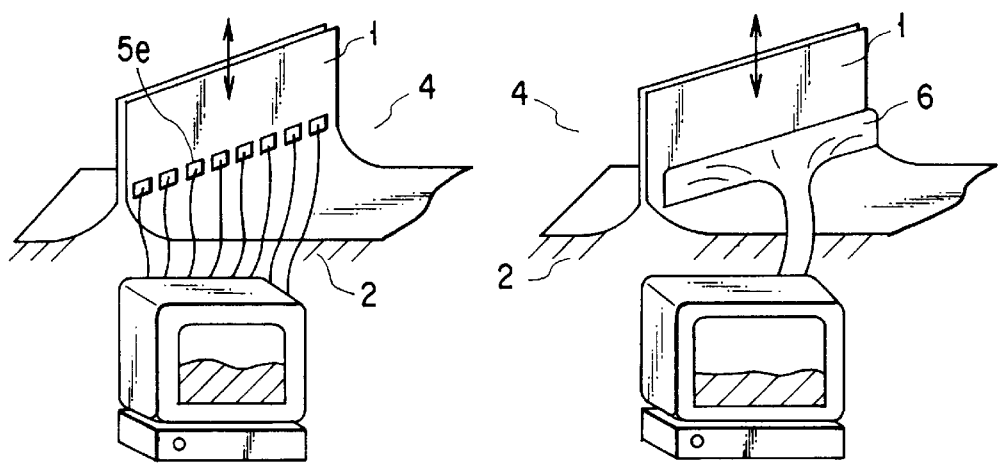
F I G. 5A  F I G. 5B
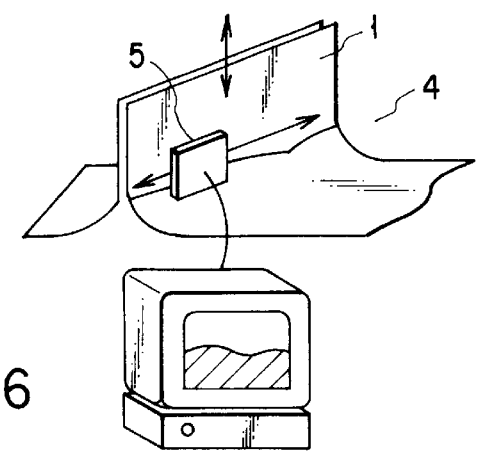
F I G. 6

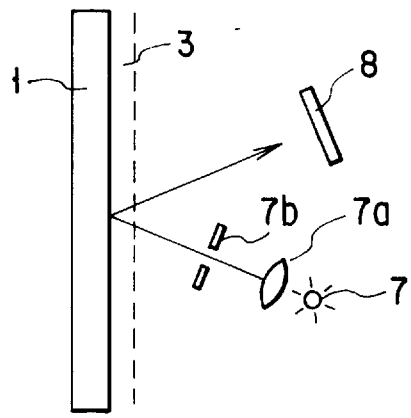
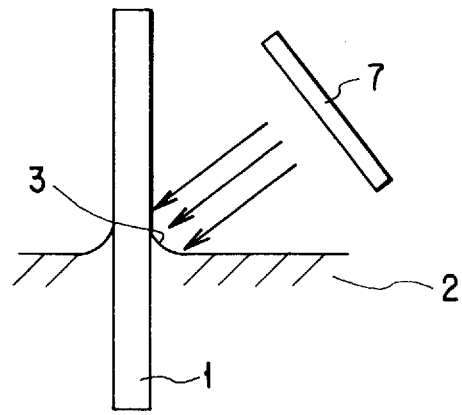
F I G. 7A              F I G. 7B
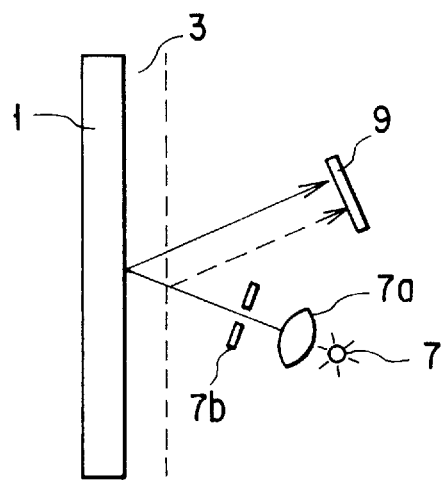
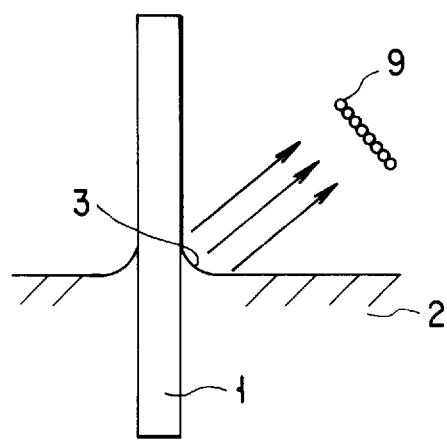
F I G. 8A              F I G. 8B

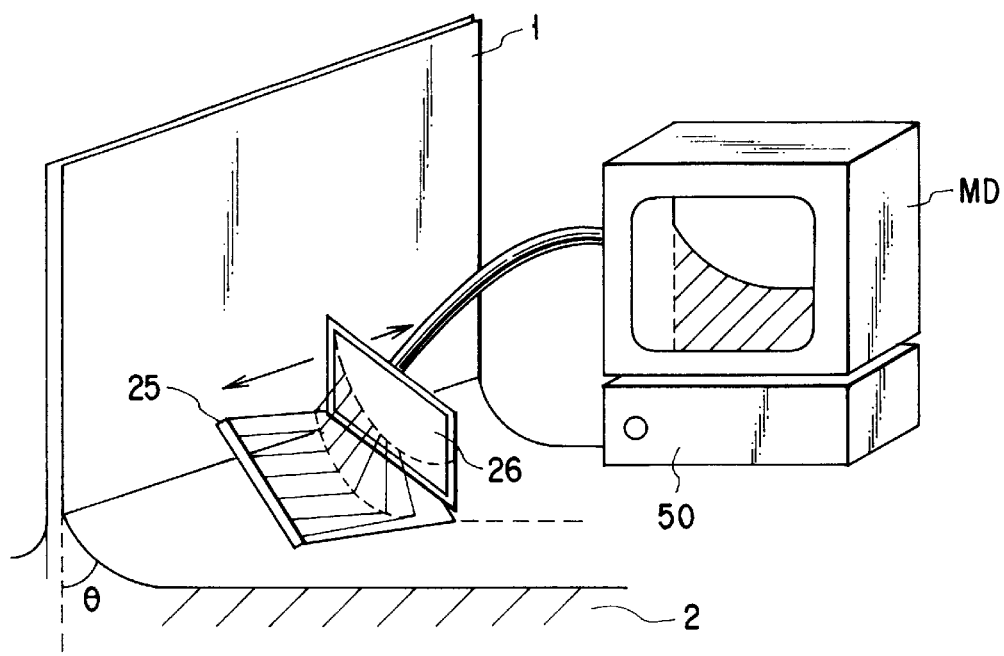
F I G. 11
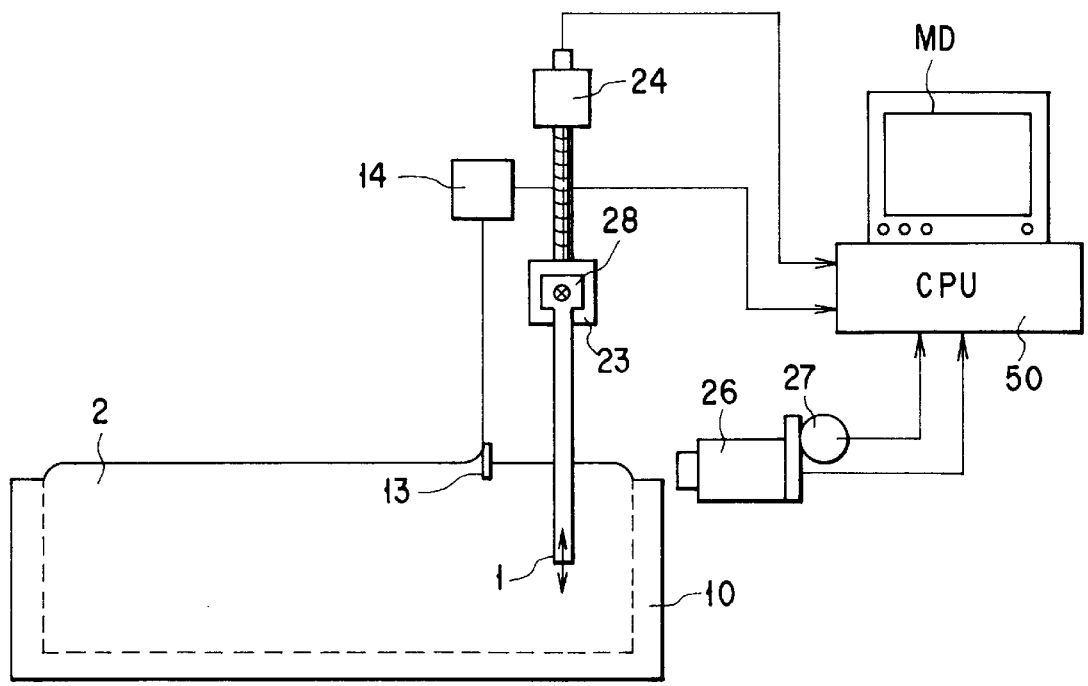
F I G. 12

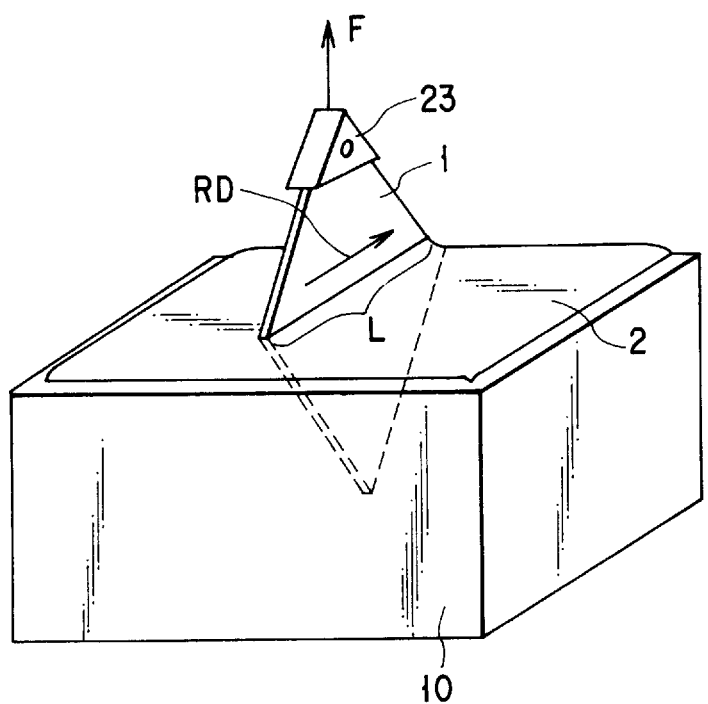
F I G. 22A
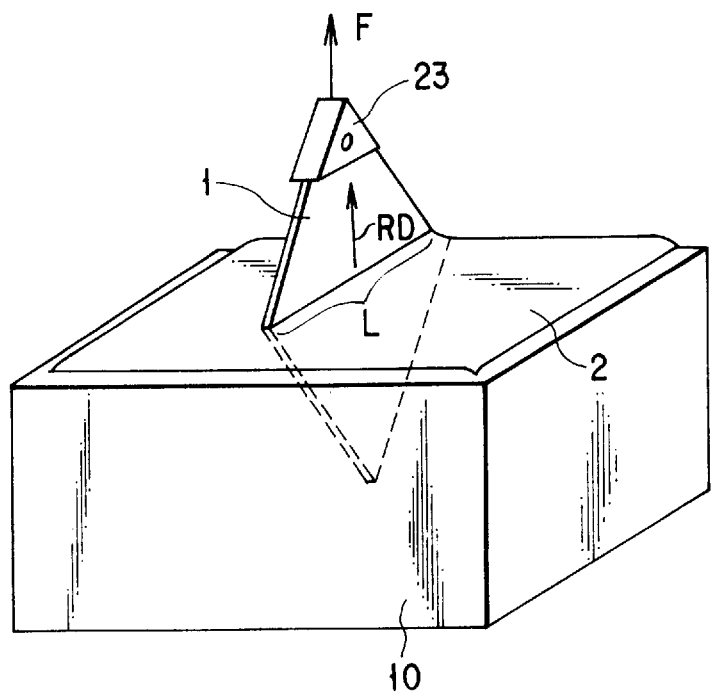
F I G. 22B

APPARATUS AND METHOD FOR MEASURING IN-PLANE DISTRIBUTION OF SURFACE FREE ENERGY

BACKGROUND OF THE INVENTION

The present invention relates to an apparatus and method for measuring in-plane distribution of surface free energy which is useful to find most appropriate conditions of every process and in facilitating the control over manufacture of a semiconductor device or a liquid crystal display. In particular, this invention relates to a technique for evaluating the surface free energy distribution of substrates after various treatments such as a washing treatment, a surface treatment, coating and removing treatments of a resist, coating and baking treatments of an alignment film or a rubbing treatment in processes of forming thin film transistors (TFT) and cells for a liquid crystal display.

When manufacturing a semiconductor device or a liquid crystal display the control of wettability of the surface of a substrate in every treatment, such as a washing treatment, a surface treatment, coating and removing treatments of a resist, is a very important requisite for obtaining a desired device structure and characteristics. For example, when a large number of semiconductor devices are arranged on a large scale substrate as in a process of forming TFTs in manufacture of a liquid crystal display, the assurance of uniformity in in-plane distribution of wettability is considered to be essential. A liquid crystal cell used in a liquid crystal display for a personal computer or a television is featured in principle in that the liquid crystal is aligned in a proper direction by controlling the surface condition of the alignment layer. The quality of the display image relates to the alignment uniformity of the liquid crystal, and the alignment uniformity relates to the uniformity of surface free energy. Therefore, it is an important subject matter to assure the uniformity of surface free energy.

As a method of evaluating the wettability of a substrate, which reflects the surface free energy of the substrate, "a droplet method" or "an exhalation method" has been employed.

The droplet method is performed by measuring the contact angle between the droplet and the surface of a substrate that may be brought about as a small amount of droplet (in most cases, water droplet) is dripped on the surface of a substrate. Although the droplet method has an advantage that the contact angle can be quantitatively measured, while it also has a disadvantage that the contact angle thus measured is point data where the droplet is dripped. Therefore, if the contact angle of the entire surface of the substrate is to be measured, the process of dripping a drop of liquid accompanied with the measurement of contact angle is required to be repeated. Such an operation however is practically difficult to obtain the in-plane distribution of the contact angle with a desired spatial frequency (e.g., the size of a pixel in the case of a liquid crystal display).

On the other hand, the exhalation method is performed by contacting the entire surface of a substrate with water vapor, followed by fine water droplets to be adhered onto the entire surface of the substrate. In this case, since the condition of adhesion of the water droplets (the contact angle, size and density of the water droplets) relates to surface free energy of the substrate, the nonuniformity of the surface free energy is detected with the naked eye by difference in light scattering property, which originates in nonuniform adhesion condition of the water droplets. Although this method has an advantage that the in-plane nonuniformity of surface free energy can be observed at a glance, it also has a disadvantage that the obtained data is qualitative, and not quantitative.

As explained above, it is difficult to obtain the quantitative data set of in-plane distribution of surface free energy, using the conventional method of evaluating surface free energy.

BRIEF SUMMARY OF THE INVENTION

Accordingly, an object of the present invention is to provide an apparatus and method for easily and quantitatively evaluating a surface free energy distribution throughout the entire surface of a substrate.

According to a first aspect of this invention, there is provided an apparatus for measuring in-plane distribution of surface free energy, comprising:

a trough containing a liquid for immersing a target substrate having a target surface, the liquid forming a liquid level;

supporting means for supporting the target substrate so as to immerse the target substrate into the liquid in the trough such that the target surface intersects with the liquid level;

measuring means for optically detecting a parameter, in a horizontal direction, representing a state of meniscus to be formed at an intersection area of the target surface with a surface of the liquid;

moving means for relatively moving the liquid level and the target substrate in a vertical direction; and distribution-forming means for forming an in-plane distribution on the target surface of measured values of the parameter or of conversion values calculated from the measured values of the parameter.

According to a second aspect of this invention, there is provided a method of measuring in-plane distribution of surface free energy, comprising the steps of:

immersing a target substrate having a target surface in a liquid;

optically measuring a parameter in a horizontal direction while keeping the target surface intersect with liquid level of the liquid, the parameter representing a state of meniscus to be formed at an intersection area of the target surface with a surface of the liquid;

relatively moving the liquid level and the target substrate in a vertical direction; and forming an in-plane distribution on the target surface of measured values of the parameter or of conversion values calculated from the measured values of the parameter.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 1A and 1B are schematic perspective views, each illustrating a method of measuring in-plane distribution of surface free energy according to this invention;

FIG. 2 is a schematic perspective view showing an in-plane distribution of contact angle;

FIG. 3 is a cross-sectional view illustrating an equilibrium of force at a triple point involving a gas, a liquid and a substrate;

FIG. 4 is a cross-sectional view illustrating a force to be worked on a substrate;

FIGS. 5A and 5B are schematic perspective views each illustrating an apparatus for measuring in-plane distribution of surface free energy, according to one embodiment of this invention;

FIG. 6 is a schematic perspective view illustrating an apparatus for measuring in-plane distribution of surface free energy, according to another embodiment of this invention;

FIGS. 7A and 7B show a plan view and vertical sectional view respectively of an apparatus for measuring in-plane distribution of surface free energy according to still another embodiment of this invention;

FIGS. 8A and 8B show a plan view and vertical sectional view respectively of an apparatus for measuring in-plane distribution of surface free energy according to still another embodiment of this invention;

FIG. 11 is a schematic perspective view illustrating a method of observing the shape of meniscus in the employment of an apparatus shown in FIGS. 7A and 7B;

FIG. 12 is a schematic view illustrating the system of an apparatus for measuring in-plane distribution of surface free energy according to Example 2 of this invention;

FIGS. 22A and 22B respectively shows a method of evaluating the rubbing conditions of an alignment layer for a liquid crystal display according to Experiment 3.

DETAILED DESCRIPTION OF THE INVENTION

Figure 9A:
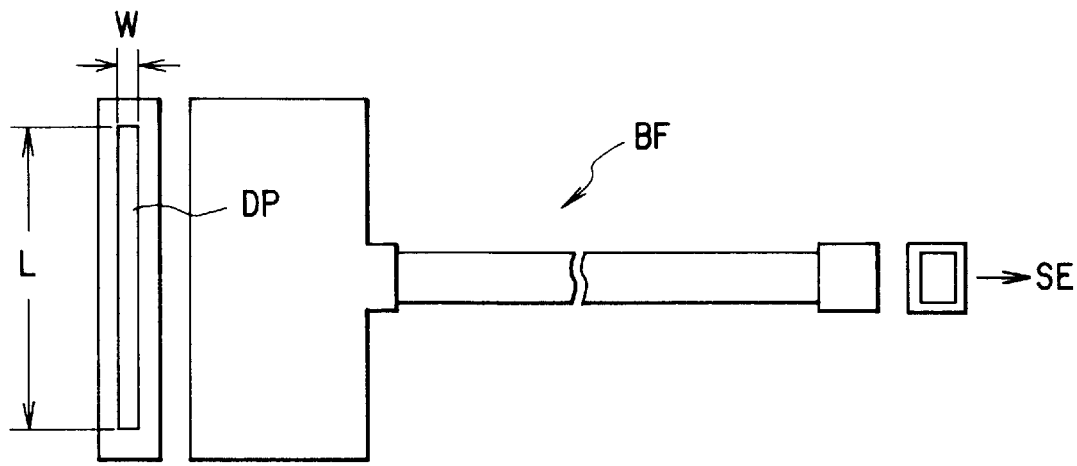
FIGS. 9A to 9C illustrate the structure of a bundle fiber to be employed as an optical fiber.

The method of this invention is featured in that the time series information of the "line" (one dimensional) of contact angle at meniscus, obtained by relatively moving a liquid level and a target substrate in a vertical direction throughout its surface, is converted into in-plane (two dimensional) contact angle distribution information.

Specifically, as shown in FIG. 1A, the target substrate 1 is immersed in a liquid 2 such as water and then the meniscus is formed on a surface of the liquid 2, followed by measuring the condition f the meniscus. For example, the contact angle θ formed at a triple point involving a gas, a liquid and a substrate is measured, thus obtaining the information on the intersection line of the target surface and the liquid surface, i.e. the linear information. Then, by relatively moving the liquid level and the target substrate in a vertical direction, quantitative data set of the condition of meniscus (the angle θ in this case) throughout the target surface of the substrate is obtained, thus making it possible to obtain quantitative data set of surface free energy distribution throughout the target surface of the substrate.

In a case where the surface free energy of the substrate is not uniform, a deformed meniscus portion FP is observed as the target substrate 1 is scanned upward or downward as shown in FIG. 1B, and this linear information set is converted into planar information, thereby obtaining the deformed portion FP, i.e. a surface irregularity PFP as shown in FIG. 2. FIG. 2 illustrates one example of visualized in-plane distribution of the contact angle θ, which is calculated from the condition of meniscus.

The measurement of contact angle is performed according to the following principle as explained below.

As shown in FIG. 3, when the target substrate 1 is immersed in the liquid 2, the shape of the liquid is altered at a triple point where three phases, i.e. a gas 4, a solid 1 (the target substrate 1) and a liquid 2 are concurrently contacted with each other. The shape of liquid at this triple point is called "meniscus" 3. When the meniscus 3 is kept in a fixed shape, the interfacial tensions among the gas 4/the solid 1; the gas 4/the liquid 2; and the liquid 2/the solid 1 are balanced at the angle θ of meniscus. The equilibrium of force at this triple point in this case can be represented by the following equations (Young's equation).

$$\gamma_{SV} = \gamma_{LV} \cos\theta + \gamma_{SL}$$

$$\cos\theta = (\gamma_{SV} - \gamma_{SL})/\gamma_{LV}$$

wherein,
$\gamma_{SL}$: interfacial tension of liquid/solid interface;
$\gamma_{LV}$: interfacial tension of liquid/vapor interface;
$\gamma_{SV}$: interfacial tension of solid/vapor interface; and
θ: contact angle of liquid/solid.

The interfacial tension is a differential of area of an interfacial free energy. Therefore, in defining the parameters of Young's equation, "interfacial tension" can be replaced with "interfacial free energy". Namely, measuring a parameter representing the shape of meniscus corresponds to measuring the balance of the interfacial energy. Further, "surface free energy" is interfacial free energy relative to vapor. Therefore, to measure a parameter representing the shape of meniscus is nothing but to measure the surface free energy, using liquid as a probe.

In this Young's equation, the contact angle θ is involved as a parameter for the shape of meniscus. Most common method of measuring this contact angle θ is to draw a tangent line along the interface of liquid from the triple point as shown in FIG. 3. It is also possible to calculate the θ as shown below by making use of an equation representing the relationship between the height "h"(=z(0)) of meniscus and the contact angle θ (Neumann, A. W., Z. Phys. Chem., 41, 339–352(1964)).

$$z(x)=[2\gamma_{LV}(1-\sin\theta)/(\rho_L-\rho_V)g]^{1/2}$$

$$\sin\theta=1-\{z(x)\}^2(\rho_L-\rho_V)g/2\gamma_{LV}$$

wherein,
- θ: contact angle;
- $\rho_V$: density of gas;
- $\rho_L$: density of liquid;
- g: acceleration of gravity;
- $\gamma_{LV}$: interfacial free energy of liquid/vapor interface;
- x: horizontal distance from and perpendicular to target surface; and
- z: vertical distance from liquid level.

In this case, (x, z) represents coordinates of a surface position of meniscus, and z(x) represents the height of that surface position of meniscus, which is separated form the target surface by a distance x, from the liquid level. Therefore, when x=0, the value of z indicates the position of the surface of meniscus on the target surface, i.e. the height from the flat liquid level to the tip end of the meniscus. Under the conditions where the composition, temperature and pressure of gas and of liquid are constant, the z(x) depends only on the value of θ.

The measurement of θ from a curvilinear shape of the surface of meniscus means a process comprising the steps of measuring a plurality set of two-dimensional coordinates along the curvature of the surface of meniscus, and calculating the θ from the two-dimensional coordinates thus measured. In this procedure, the value of $\gamma_{LV}$ can be simultaneously determined. The accuracy of measurement of θ may be improved by making use of a substrate for measuring $\gamma_{LV}$ (Wilhelmy Plate to be discussed hereinafter) and by substituting the found value for $\gamma_{LV}$.

Alternatively, the contact angle θ may be indirectly measured by making use of a method to measure the tractive force of the substrate. This method of determining the contact angle θ from the force F for pulling the substrate will be explained below.

As shown in FIG. 4, when the target substrate 1 is kept remained in a fixed immersed state in a liquid 2, all of the forces are balanced. The forces worked on the substrate at this moment can be expressed by the following equation (Neumann's equation).

$$F=Mg-\delta V+L\gamma_{LV}\cos\theta$$

wherein,
- F: upward force for keeping equilibrium;
- Mg: gravity of substrate;
- δV: buoyancy of substrate;
- $\gamma_{LV}$: interfacial tension at liquid/vapor interface;
- θ: contact angle of liquid/substrate; and
- L: circumferential length of substrate immersed in water.

In this equilibrium equation of force, Mg and L are constants, and δV is a constant where a immersed volume of the substrate is constant, while $\gamma_{LV}$ also becomes a constant under the conditions where the liquid, the composition of gas (partial pressure) and temperature are all fixed. Therefore, only F is dependent on the contact angle θ. Accordingly, the contact angle θ can be determined by simply measuring the force F.

The method of measuring tractive force of the substrate can be also utilized for determining not only the contact angle θ but also the interfacial tension $\gamma_{LV}$. In this case, it is desirable that a substrate (Wilhelmy Plate) for measuring the interfacial tension $\gamma_{LV}$ is separately prepared and mounted on an apparatus for measuring in-plane distribution of surface free energy according to this invention.

Followings are descriptions on the fundamental construction of the hardware which is required for the measurement of the contact angle.

First of all, requirements for the liquid and gas which are indispensable for the measurement of contact angle will be discussed. As will be understood from the principle of measurement, the liquid and gas are simply probing means for measuring the surface free energy of a target substrate. Therefore, the principle of measurement according to this invention would not be restricted by the kinds of liquid and gas to be employed in this invention. However, in view of keeping the gas atmosphere constant, the liquid should preferably be selected from those having a low volatility. If a liquid which is high in volatility is to be employed, a unit for keeping the atmosphere of gas (temperature and partial pressure) constant is required to be employed. As for the gas, an inert gas is preferable in view of avoiding any change in $\gamma_{SV}$ which might be resulted from the adsorption of gas onto the substrate. Furthermore, in view of easiness in handling, the employment of water as the liquid and the employment of $N_2$ or air as the gas are preferable. As for the liquid, it is also possible to employ alkane, ethylene glycol, mercury and liquid crystal. The liquid should desirably be connected to a temperature controller for keeping the temperature of liquid constant. Followings are examples of liquid which can be employed in this invention and whose interfacial tension with air at the normal pressure is known.

TABLE 1

(Interfacial tension at 20° C. of liquid to be employed in an apparatus for measuring in-plane distribution of surface free energy of this invention)

| Compounds | Interfacial tension (dyne/cm) |
| --- | --- |
| Acetone | 23.32 |
| Isobutyl alcohol | 22.8 |
| Isopentane | 14.97 |
| Ethanol | 22.27 |
| Ethyl cyclohexane | 25.7 |
| Ethyl benzene | 29.04 |
| Ethyl methyl ketone | 24.6 |
| 1-octanol | 26.71 |
| 2-octanol | 25.83 |
| 3-octanol | 25.05 |
| 4-octanol | 25.43 |
| Octane | 21.76 |
| o-xylene | 30.03 |
| m-xylene | 28.63 |
| p-xylene | 28.31 |
| o-chlorotoluene | 33.44 |
| 1-chlorohexane | 26.21 |
| Chlorobenzene | 33.28 |
| 1-chloropentane | 25.06 |
| Chloroform | 27.28 |
| Ethyl acetate | 23.8 |
| Vinyl acetate | 23.95 |
| o-diethylbenzene | 30.3 |
| m-diethylbenzene | 28.2 |
| p-diethylbenzene | 29.0 |

TABLE 1-continued (Interfacial tension at 20° C. of liquid to be employed
in an apparatus for measuring in-plane distribution of
surface free energy of this invention)

| Compounds | Interfacial tension (dyne/cm) |
|---|---|
| 1,4-dioxane | 33.55 |
| 1,1-dichloroethane | 24.75 |
| Cyclohexanol | 34.5 |
| Cyclohexane | 24.95 |
| Cycloheptanone | 35.38 |
| Dimethyl sulfoxide | 43.54 |
| Ethyl bromide | 24.15 |
| Butyl bromide | 26.33 |
| Propyl bromide | 25.85 |
| 1-decanol | 27.32 |
| Decane | 23.92 |
| 1-dodecanol | 26.06 |
| Toluene | 28.53 |
| 1-nonanol | 26.41 |
| 3-nonanone | 27.4 |
| Nonane | 22.92 |
| Pyridine | 38.0 |
| Butylbenzene | 29.23 |
| Butyl fluoride | 17.72 |
| Fluorobenzene | 27.71 |
| 1-propanol | 23.70 |
| 2-propanol | 21.35 |
| 1-bromohexane | 28.04 |
| Bromobenzene | 36.34 |
| 1-bromopentane | 27.29 |
| Bromoform | 41.91 |
| 1-hexanol | 24.48 |
| Hexamethyl disiloxane | 15.7 |
| Hexane | 18.42 |
| 1-heptanol | 24.42 |
| Heptane | 20.31 |
| Benzene | 28.86 |
| 1-pentanol | 25.60 |
| Pentyl benzene | 29.65 |
| Methanol | 22.55 |
| Ethyl iodide | 28.83 |
| Butyl iodide | 29.15 |
| Propyl iodide | 29.28 |
| Methyl iodide | 30.14 |
| 1-iodohexane | 29.93 |
| Water(1) | 72.75 |
| Mercury(2) | 484.2 |

(NOTE)
(1) "Landolt-Bornsteln Tabellen"; 6 Aufl., H Band. 3 Teil. Springer-Verlag (1956).
(2) C. Kemball. Trans.Faraday Soc., 42. 526 (1946).
Others are all based on O. R. Quayle. Chem.Rev., 53. 439 (1953).

Furthermore, if three or more kinds of liquid, whose surface tension in terms of dispersion force component ($\gamma_L^d$), dipole component ($\gamma_L^P$) and hydrogen bond component ($\gamma_L^h$) being already known, are employed to measure the contact angle distribution of each liquid with respect to the same target substrate, it is possible to determine the dispersion force component ($\gamma_L^d$), dipole component ($\gamma_L^P$) and hydrogen bond component ($\gamma_L^h$) of the surface tension of the target substrate. Examples of the liquid useful for this purpose are n-hexane, n-hexadecane, a-bromonaphthalene, methylene iodide, formamide, water, etc. In particular, the employment of three kinds of liquid, i.e. water, methylene iodide and a-bromonaphthalene is most effective in practical view point. Table 3 shows the aforementioned components of surface free energy at 20° C. of these three kinds of liquid.

TABLE 2

| | Surface free energy (dyne/cm) | | | |
|---|---|---|---|---|
| Liquid | $\gamma_L$ | $\gamma_L^d$ | $\gamma_L^P$ | $\gamma_L^h$ |
| Water | 72.8 | 29.1 | 1.3 | 42.4 |
| Methylene iodide | 50.8 | 46.8 | 4.0 | 0.0 |
| a-bromonaphthalene | 44.6 | 44.4 | 0.2 | 0.0 |

Next, requirements for the material to be used for the trough will be explained.

Fundamentally, a material which is free from elution of impurities (in particular, metallic ions) can be employed as a material for the trough. Specifically, a trough coated on its inner surface with a fluoric material or fluorine resin may be preferable for use. Additionally, an alkali-free glass or quartz glass which has been treated with silane for instance to turn it into a hydrophobic glass may also be useful. Since meniscus is very sensitive to vibration, the measurement thereof is performed while the trough is mounted on a vibration proof table. Furthermore, in view of continuously maintaining the clean surface of liquid, a liquid level-cleansing unit which is adapted to pump up a contaminated surface of liquid should preferably be mounted on the trough.

Next, the mechanism for moving the substrate-suspension unit up and down will be explained.

This substrate-suspension unit is adapted to hold the substrate by the upper portion thereof and connected to a motor so that the substrate can be ascended or descended while being held by the substrate-suspension unit. The moving speed of the substrate during the measurement should be kept constant in principle. Preferably, the moving speed of the substrate should be not more than 100 mm/sec., and the deviation of the moving speed should preferably be controlled within ±0.1%.

Next, the display parameter of the surface free energy distribution will be explained.

Since the scanning of the relative position of the meniscus to the substrate is performed while the substrate is moved up and down, the contact angles measured are, speaking strictly, dynamic ones. The contact angle $\theta_a$ to be measured during the descending of the substrate is called "advancing contact angle", while the contact angle $\theta_r$ to be measured during the ascending of the substrate is called "receding contact angle". Generally speaking, the advancing contact angle is larger than the receding contact angle, i.e. $\theta_a > \theta_r$. As for the method of displaying the in-plane distribution of surface free energy according to this invention, either $\theta_a$ or $\theta_r$ is measured at first and then an in-plane distribution of either $\theta_a$ or $\theta_r$, or of either $\cos \theta_a$ or $\cos \theta_r$ may be displayed. Alternatively, an in-plane distribution of an average value of difference between the advancing contact angle and the receding contact angle, i.e.;

($\cos \theta_r - \cos \theta_a$)/2 or $\arccos[(\cos \theta_r - \cos \theta_a)/2]$ may be displayed. If the value of $\gamma_{LV}$ is already known, the in-plane distribution may be displayed by way of any one of three parameters, i.e.;

$\gamma_{LV} \cos \theta_r$, $\gamma_{LV} \cos \theta_a$, or $\gamma_{LV}(\cos \theta_r - \cos \theta_a)/2$.

Next, a method of calculating the dispersion force component ($\gamma_L^d$), dipole component ($\gamma_L^P$) and hydrogen bond component ($\gamma_L^h$) of the surface tension of the target substrate will be explained. The details on the method of formulating the calculating formula should be referred to the document, "For the Understanding of Surface Tension", M. Imoto, Kobunshi Kankokai (1992).

$$\gamma_L(1+\cos\theta)=2(\gamma_L^d\times\gamma_S^d+\gamma_L^P\times\gamma_S^P+\gamma_L^h\times\gamma_S^h)$$

wherein, $\gamma_L^d$: surface tension of liquid (dispersion force component);

$\gamma_L^P$: surface tension of liquid (dipole component);

$\gamma_L^h$: surface tension of liquid (hydrogen bond component);

$\gamma_S^d$: surface tension of solid (dispersion force component);

$\gamma_S^P$: surface tension of solid (dipole component); and $\gamma_S^h$: surface tension of solid (hydrogen bond component).

It is also possible to calculate the $\gamma_L^d$, $\gamma_L^P$ and $\gamma_L^h$ of each coordinate of the target substrate, and then display the in-plane distribution each of the $\gamma_{Sd}$, $\gamma_S^P$ and $\gamma_S^h$.

With regard to the method of measuring the contact angle θ, there are two methods as explained above, i.e. a method of measuring the height of meniscus, and a method of measuring the shape of meniscus (measuring a plurality set of two-dimensional coordinates along the curvature of the surface of meniscus). These methods may be performed, with an employment of an optical measuring device, by observing the contrast in brightness of the meniscus.

If the optical measuring device is provided with an optical detector extending along the whole width of the target substrate in the method of measuring the height of the meniscus, a linear information on the height of the meniscus can be obtained at a time. FIG. 5A illustrates a system wherein a plurality of optical sensors 5e are arranged parallel with the direction of edge line of the meniscus (i.e. a dominant direction in the substantially horizontal line to be defined by the edge of meniscus), and the information obtained via these optical sensors 5e is image-processed by a monitor display MD, whereby obtaining a linear information at a time. On the other hand, FIG. 5B illustrates a system wherein optical fibers 6 are arranged parallel with the direction of edge line of the meniscus, and a linear information obtained via these optical fibers 6 is fed at a time to a monitor display MD provided with optical sensors.

If the optical measuring device is provided with an optical detector of spot type in the method of measuring the height of the meniscus, the optical detector is moved along the edge line of the meniscus so as to successively obtain a "point" information on the height of the meniscus, whereby ultimately obtaining a linear information. FIG. 6 illustrates one embodiment of such a system wherein a single optical sensor 5 connected to a monitor display MD is sustained by a holder which is movable in the transverse direction, thereby making it possible to scan the edge line of the meniscus.

On the other hand, the method of measuring the shape of the meniscus can be performed for example by obliquely irradiating a light from one side to the surface of meniscus, and then detecting the reflected light from the surface of meniscus by making use of an optical measuring device.

FIGS. 7A and 7B show a plan view and vertical sectional view respectively of such an optical measuring device as one embodiment. Referring to FIGS. 7A and 7B, a line light source 7 is arranged such that it is directed in perpendicular to the edge line of the meniscus and inclined at an angle of 45° to the surface of the liquid. Additionally, an optical sensor 8 is disposed so as to receive a reflected light from the surface of the meniscus. These line light source 7 and optical sensor 8 are integrally and simultaneously moved along the edge line of the meniscus, thereby making it possible to obtain a linear information. In this case, with a view to convert the light from the line light source 7 into parallel rays and at the same time to limit the irradiation of light only to the portion to be detected, a collimator lens 7a and a slit 7b are disposed. FIGS. 8A and 8B show a plan view and vertical sectional view respectively of an optical measuring device where a PSD array 9 to be explained hereinafter is disposed in place of the aforementioned optical sensor 8.

As for the detecting element of the optical measuring device, a photodiode may be useful. Specifically, a CCD (Charge Coupled Device) which is a solid image sensor comprising a two-dimensionally divided photodiode; a CPD (Charge Priming Device); a MOS (Metal Oxide Semiconductor); or a PSD (Position Sensitive Detectors) may be employed.

If a PSD array is employed as shown in FIGS. 8A and 8B, a line light source having almost the same size as that of the PSD array is preferably disposed in perpendicular to the direction of the edge line of meniscus. In this case, each of the PSDs is arranged such that the longitudinal direction thereof is kept parallel with the direction of the edge line of meniscus, and the line light source and the two-dimensional PSD are integrally moved along the direction of the edge line. In this case also, a supporting member for the detecting element is connected to a motor, and the scanning with the detecting element is performed by driving the motor at a constant speed.

Figure 9B:
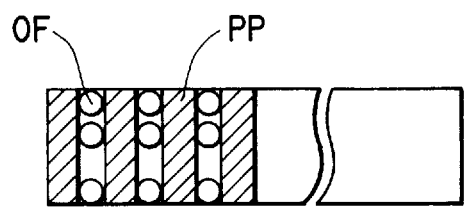
Figure 9C:
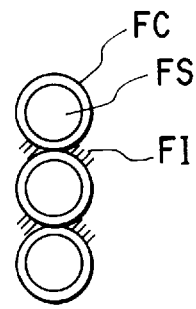

As for the optical fiber, a bundle fiber BF as shown in FIGS. 9A to 9C may be employed. FIG. 9A shows schematical views of the entire structure of the bundle fiber BF; FIG. 9B shows a partially sectioned enlarged vertical front view illustrating the incident port DP at the tip end of the bundle fiber BF; and FIG. 9C shows a much more enlarged vertical front view illustrating the arrangement of optical fibers OF in the incident port DP.

As shown in these FIGS., a plurality of optical fibers OF are kept in a case CA provided with the incident port DP. This incident port DP, having a length of L and a width of W, is arranged such that the longitudinal edge thereof having a length of L becomes parallel with the meniscus. The opposite end of each optical fiber OF is connected to an optical sensor SE. The optical fibers OF are partitioned with partitioning plates PP so as to be regularly arrayed, and are fixed in place with a filler FI. The marks FS and FC represent the core and clad of optical fiber, respectively.

It is required in this invention that the spatial frequency in the direction of height of liquid level is as high as possible. However, with regard to the spatial frequency in the horizontal direction, the spatial frequency thereof is inherently restricted in principle by the influence from the gravity of water therearound. Therefore, any substantial problem would be raised even if the optical fibers are thinned out in the horizontal direction by replacing some of them with the partitioning plates PP.

As for the optical sensor, the CCD, CPD and MOS are useful in particular among the aforementioned photodiodes. As for the light source, one which is capable of irradiating the meniscus entirely can be preferably employed. A cylindrical lens may be additionally interposed for the purpose of focusing between the optical fibers and the meniscus and along the edge line of meniscus, thereby improving the spatial frequency in the direction of height of meniscus. The length of the optical fibers may be adjusted in conformity with the length of the target substrate to be measured. The width of the optical fiber should desirably be not less than 100 μm.

EXAMPLE 1

Figure 10:
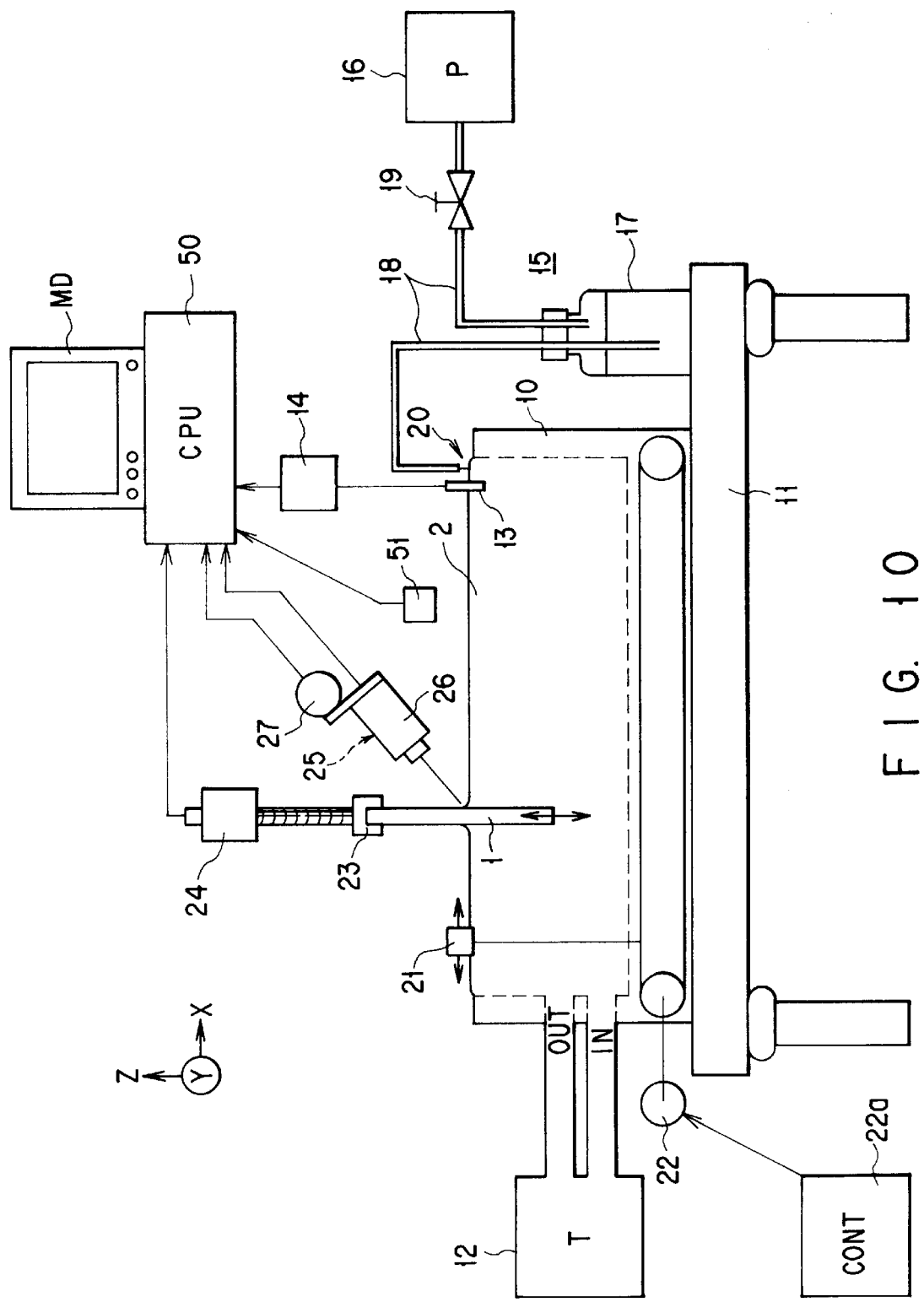
FIG. 10 is a schematic view illustrating the system of an apparatus for measuring in-plane distribution of surface free energy according to Example 1 of this invention.

FIG. 10 illustrates the construction of an apparatus for measuring in-plane distribution of surface free energy of Example 1 according to this invention. Followings are explanations on the components constituting this apparatus.

A trough 10 is mounted on a vibration proof table 11 having a horizontal mounting surface. This trough 10 is formed of an aluminum block which has been scooped out to form a hollow portion, the inner surface of which is coated with a fluorine plastic. The trough 10 is filled with a liquid 2 consisting of pure water (or a deionized water), and communicated with a liquid temperature controller unit 12. This liquid temperature controller unit 12 is provided with a temperature controlling function as well as a liquid circulating function, thereby making it possible to accurately keep the temperature of the trough 10 to a fixed temperature with an error of ±0.5° C.

Wilhelmy Plate 13 is a plate for measuring the surface free energy of a liquid. As a material for the Wilhelmy Plate 13, a material exhibiting the complete wettability (contact angle $\theta=0°$) such as a filter paper or a ground glass can be employed. The interfacial free energy at a liquid/vapor interface ($\gamma_{LV}$) can be determined by measuring at first the force to be worked on the Wilhelmy Plate 13 by making use of a differential transformer (or a strain gauge) 14, and then by calculating the $\gamma_{LV}$ by making use of the following formula wherein $\theta=0°$ is substituted in aforementioned Neumann's equation;

$$F = Mg - \delta V + L\gamma_{LV}$$

wherein, $\gamma_{LV}$: surface free energy of liquid;
F: force worked on differential transformer where Wilhelmy Plate is immersed in water;
Mg: gravity of substrate;
$\delta V$: buoyancy of substrate; and
L: circumferential length of substrate immersed in water.

If a filter paper is employed, the $\delta V$ can be disregarded ($\delta V=0$).

The liquid level-washing unit 15 is formed of a combination of a rotary pump 16, a bottle 17 and a nozzle 18. When a valve 19 is opened, the nozzle 18 functions to suck up the surface portion of liquid together with soil if any, and the sucked liquid is collected in the liquid bottle 17. It is possible to adjust the height of liquid level by adjusting the level of a liquid face-washing nozzle 20. Preferably, the height of liquid face is controlled such that the liquid face is swelled over the edge of the trough by a height of 1 to 3 mm (by taking advantage of the surface tension of water).

The washing of liquid face is carried out immediately before immersing the substrate. In the process of washing, a partitioning plate 21 is advanced in front of the Wilhelmy Plate 13 by controlling an X-axis motor 22 through a controller 22a, and then the surface portion of liquid is sucked in together with soil, if any, by making use of the liquid face-washing nozzle 20. After confirming that the $\gamma_{LV}$ of water that has been calculated from the force worked on the Wilhelmy Plate 13 becomes close to the value of Table 1, i.e. (72.75) (which means that soil has been removed), the partitioning plate 21 is again moved close to the left side of the trough 10 by means of the X-axis motor 22, and then the measurement is initiated.

The target substrate 1 is held by its upper end by means of a substrate-holding unit 23. This substrate-holding unit 23 is connected to a Z-axis motor 24, and the movement of the Z-axis motor 24 is controlled by a controller.

The shape of meniscus can be observed through the combination of a line light source 25 with a CCD 26 as shown in FIG. 11. Namely, the line light source 25 and the CCD 26 are connected as an integral body to a Y-axis motor 27, which is adapted to be moved simultaneously with the movement of the Z-axis motor 24. The scanning speed in the direction of Y-axis is set such that it is sufficiently faster than the scanning speed in the direction of Z-axis. The information on the location as measured in the directions of Y-axis and Z-axis, as well as the information on the shape of meniscus at this location are sequentially transmitted to a CPU 50 provided with an image processor, where a contact angle $\theta$ is calculated according to the following equation.

$$z(x) = [2\gamma_{LV}(1-\sin\theta)/(\rho_L - \rho_V)g]^{1/2}$$

The liquid level ($z=0$) which constitutes the basis for calculating the $z(x)$ can be determined by measuring the height of the horizontal plane of the liquid level by making use of a laser displacement gauge 51. In this example, it is preferable to connect the laser displacement 51 to the CCD 26 in a integrated state, so as to compensate for shaking of the Y-axis motor 27.

The linear information of the contact angle $\theta$ which is calculated from the signal from the CCD 26 is successively accumulated in the vertical direction according to the scanning operation in the direction of Z-axis. Then, based on this accumulated linear information, the CPU 50 functions to form an in-plane distribution of the contact angle $\theta$ all over the target surface of the substrate 1, the result being displayed on the monitor display MD.

EXAMPLE 2

FIG. 12 illustrates the construction of an apparatus for measuring in-plane distribution of surface free energy of Example 2 according to this invention. Followings are explanations on the components constituting this apparatus.

The construction of each of the partitioning plate 21, the controlling system involved, the liquid temperature controller unit 12, the liquid level-washing unit 15, the vibration proof table 11, Wilhelmy Plate 13 and the differential transformer 14 is the same as that employed in Example 1. Therefore, explanations on these apparatus are omitted herein. As for liquid, water is employed as in the case of Example 1.

Figure 13:
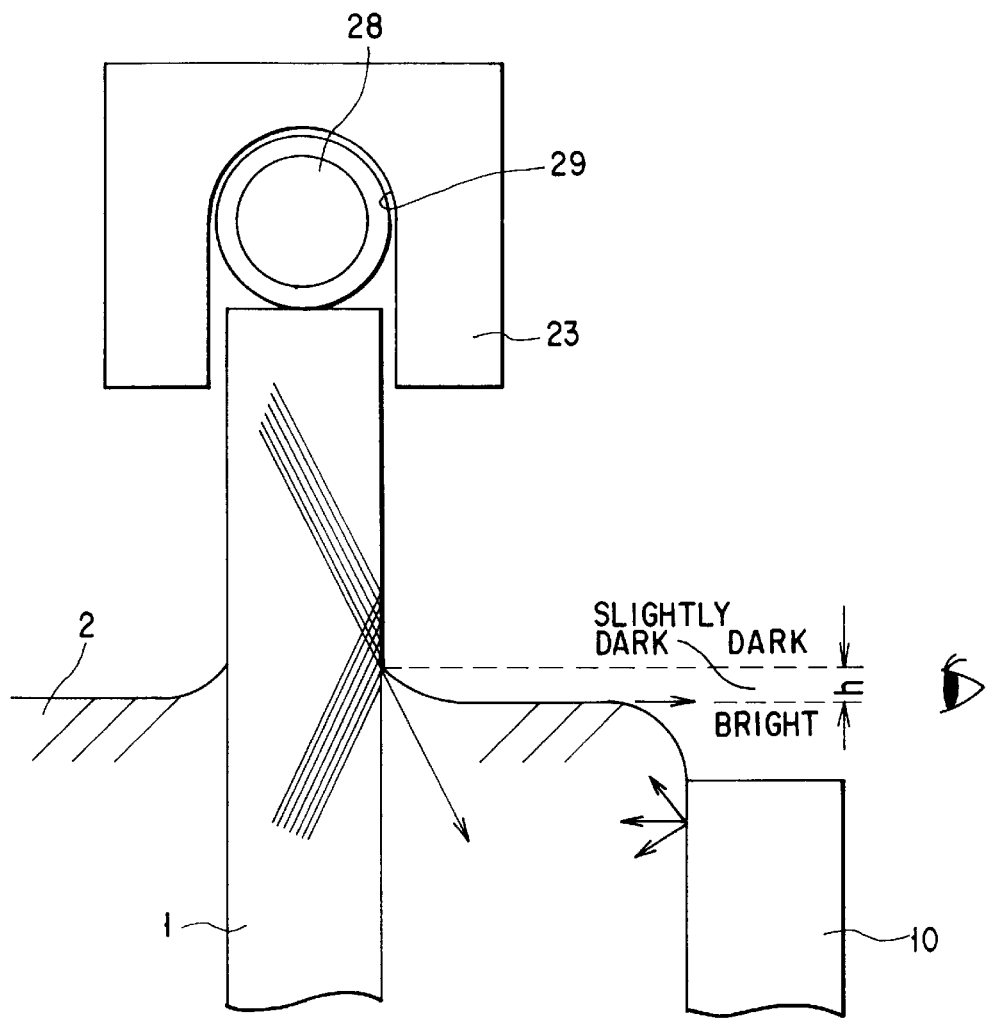
FIG. 13 is a cross-sectional view illustrating a method of measuring the height of meniscus in the employment of an apparatus shown in FIG. 12.
Figure 14:
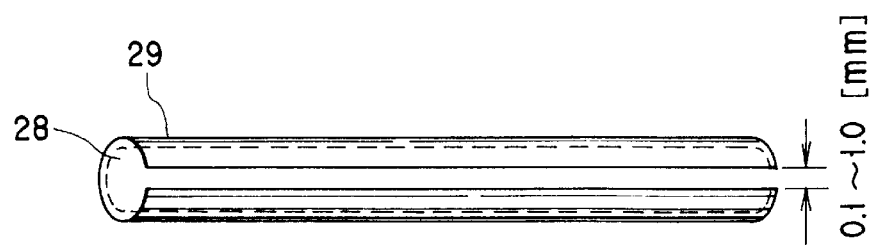
FIG. 14 is a perspective view illustrating the construction of a tubular fluorescent lamp to be employed as a linear light source for use in the apparatus shown in FIG. 13.

In this example, the height of meniscus is measured first of all in the mechanism of measuring the contact angle. Other mechanisms are the same as those of Example 1. The method of measuring the height of meniscus is illustrated in FIGS. 12, 13 and 14. As for the light source, a line light source having a length substantially equivalent to that of the substrate is employed. The line light source employed in this example comprises a cold cathode fluorescent lamp 28 having a diameter of 2 to 4 mm, and a slitted reflective cover 29 having a slit of 0.1 to 1.0 mm in width and wound around the fluorescent lamp 28. As for the substrate, a transparent substrate such as a glass substrate may be employed.

When light from the line light source is introduced from an edge portion of the substrate, a difference in total reflection angle is generated due to a difference in refractive index between the air/substrate interface and the water/substrate interface (i.e., n(air)=1.0; n(glass)=1.5; and n(water)=1.33). Therefore, This difference in total reflection angle is taken advantage of, thereby obtaining a difference of contrast, thus measuring the height of meniscus. In this case, with a view to enhance the contrast, the trough may be manufactured by scooping out a white material such as fluorine plastic (e.g., Teflon, Polyflon, etc.).

The information on the location as measured in the directions of Y-axis and Z-axis, as well as the information on the height of meniscus at this location are sequentially transmitted to a CPU 50 provided with an image processor, where a contact angle θ is calculated according to the following equation.

$$\sin \theta = 1 - h^2(\rho_L - \rho_V)g/2\gamma_{LV}$$

wherein,
- h: height of meniscus;
- $\rho_V$: density of gas;
- $\rho_L$: density of liquid;
- g: acceleration of gravity; and
- $\gamma_{LV}$: interfacial free energy of liquid/vapor interface.

The linear information of the contact angle θ which is calculated from the signal from the CCD 26 is successively accumulated in the vertical direction according to the scanning operation in the direction of Z-axis. Then, based on this accumulated linear information, the CPU 50 functions to form an in-plane distribution of the contact angle θ all over the target surface of the substrate 1, the result being displayed on the monitor display MD.

EXAMPLE 3

Figure 15:
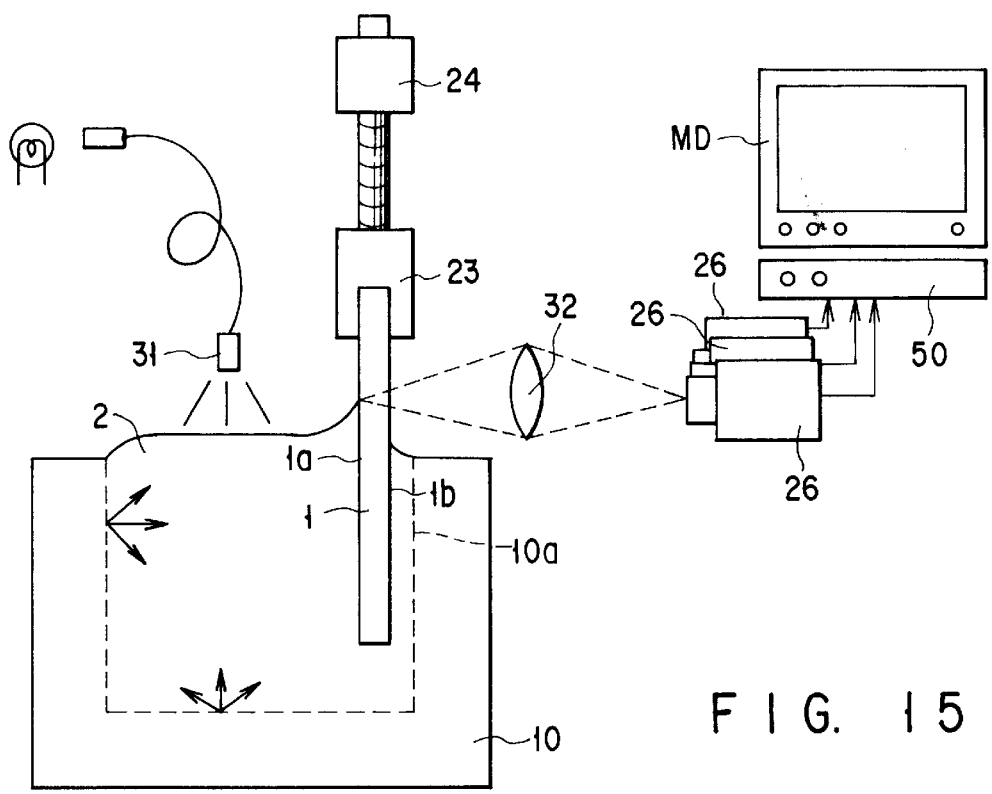
FIG. 15 is a schematic view illustrating the system of an apparatus for measuring in-plane distribution of surface free energy according to Example 3 of this invention.

FIG. 15 illustrates the construction of an apparatus for measuring in-plane distribution of surface free energy of Example 3 according to this invention. Followings are explanations on the components constituting this apparatus.

As in the case of Example 2, the height of the meniscus is measured first of all in the mechanism of measuring the contact angle. Other mechanisms are the same as those of Example 1. The apparatus having the same construction as employed in Example 2 except the optical system for measuring the meniscus is employed in this example. As for the material for the trough, Teflon which is excellent in hydrophobic nature and white in color is employed. As for the light source, a light source 31 comprising an optical fiber is employed.

In this example, the liquid face is swelled over the edge of the trough 10 by taking advantage of the surface tension of the liquid. Further, the distance between the back surface 1b (opposite to the target surface 1a) of the target substrate 1 and the Teflon wall 10a is controlled to within several millimeters, thereby causing the height of meniscus on the back surface side to become lower than the height of meniscus on the target surface side due to an influence by the hydrophobic wall 10a. As a result, it is possible to observe the meniscus of the target surface (1a) side through the transparent target substrate from the back surface (1b) side.

Furthermore, the diffused reflection from the wall of white raw material as well as the total reflection at the substrate/liquid interface are taken advantage of, i.e. an increase in brightness of liquid side is taken advantage of, thereby obtaining a sufficient contrast. Moreover, a plurality of CCDs 26 are disposed, thus making it possible to input at a time the information on the height of meniscus. By the way, a lens 32 is interposed between each CCD 26 and the target substrate 1.

The information on the height of meniscus is sequentially transmitted from the CCDs 26 to the CPU 50 provided with an image processor, and processed in the same manner as in Example 2, thus forming an in-plane distribution of the contact angle θ all over the target surface of the substrate 1.

EXAMPLE 4

Figure 16:
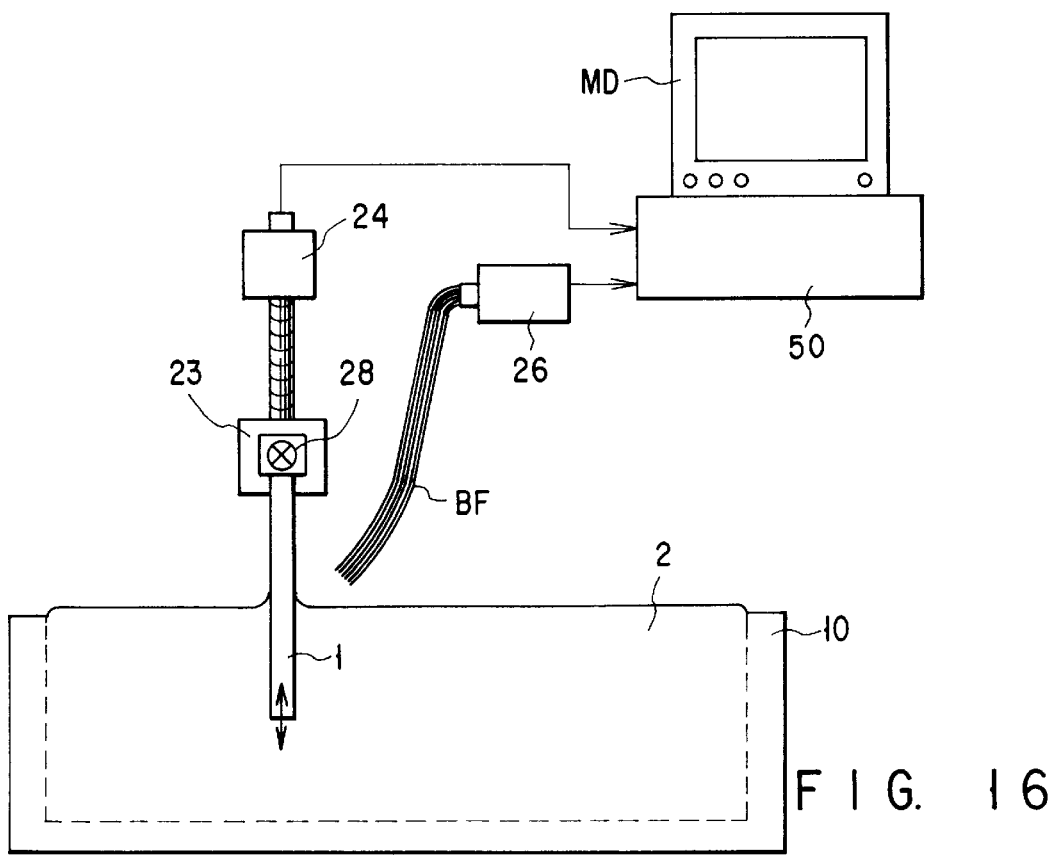
FIG. 16 is a schematic view illustrating the system of an apparatus for measuring in-plane distribution of surface free energy according to Example 4 of this invention.

FIG. 16 illustrates the construction of an apparatus for measuring in-plane distribution of surface free energy of Example 4 according to this invention. Followings are explanations on the components constituting this apparatus.

The construction of this apparatus is the same as that employed in Example 2 except that the input of CCD is performed through an optical fiber. As for the optical fiber, a bundle fiber BF as shown in FIGS. 9A, 9B and 9C are employed. The length of the optical fiber is made equal to the length of the target substrate 1, and width of the optical fiber is set to 1 mm.

The information on the location as measured in the direction of Z-axis, as well as the information on the height of meniscus at this location are sequentially transmitted to an image processor, where a contact angle θ is calculated according to the following equation.

$$\sin \theta = 1 - h^2(\rho_L - \rho_V)g/2\gamma_{LV}$$

wherein,
- h: height of meniscus;
- $\rho_V$: density of gas;
- $\rho_L$: density of liquid;
- g: acceleration of gravity; and
- $\gamma_{LV}$: interfacial free energy of liquid/vapor interface.

EXAMPLE 5

Figure 17:
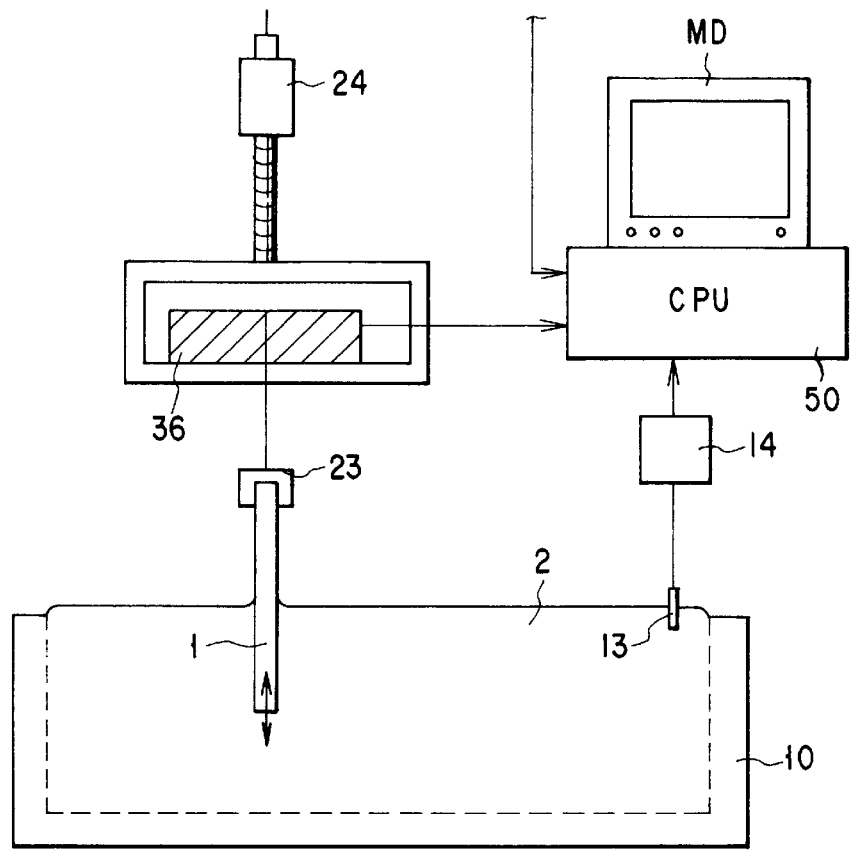
FIG. 17 is a schematic view illustrating the system of an apparatus for measuring in-plane distribution of surface free energy according to Example 5 of this invention.

FIG. 17 illustrates the construction of an apparatus for measuring in-plane distribution of surface free energy of Example 5 according to this invention. Followings are explanations on the components constituting this apparatus.

The construction of each of the partitioning plate 21, the controlling system involved, the liquid temperature controller unit 12, the liquid level-washing unit 15, the vibration proof table 11, Wilhelmy Plate 13 and the differential transformer 14 is the same as that employed in Example 1. Therefore, explanations on these apparatus are omitted herein. As for liquid, water is employed as in the case of Example 1.

In this example, the force worked on the target substrate 1 is measured first of all in the mechanism of measuring the contact angle. Other mechanisms are the same as those of Example 1. The measurement of the force worked on the target substrate 1 is performed by measuring the load weighed on an electronic balance 36 connected to the substrate-suspending unit 23. The electronic balance 36 is connected entirely to the Z-axis motor 24. The movement of the Z-axis motor 24 is controlled by a controller.

The information on the location as measured in the direction of Z-axis, as well as the information on the force F worked on the substrate are sequentially transmitted to an image processor.

Then, the immersing direction of the substrate is rotated by an angle of 90° and then the same measurement as mentioned above is repeated. The results measured with respect to the force F is applied to the following equation (Neumann's equation), thereby calculating the contact angle θ.

$$F = Mg - \delta V + L\gamma_{LV} \cos \theta$$

wherein,
- Mg: reading of electronic balance where substrate is kept in air;
- δV: (immersed volume of substrate in water)×{(density of water)−(density of substrate)};
- F: force worked on substrate (reading of electronic balance);

L: circumferential length of substrate immersed in water; and $\gamma_{LV}$: surface tension of liquid.

Following Experiments 1 to 3 illustrate examples wherein an apparatus for measuring in-plane distribution of surface free energy according to this invention is used in a failure analysis in the line of manufacturing a liquid crystal display cell.

EXPERIMENT 1

Figures 18A, 18B:
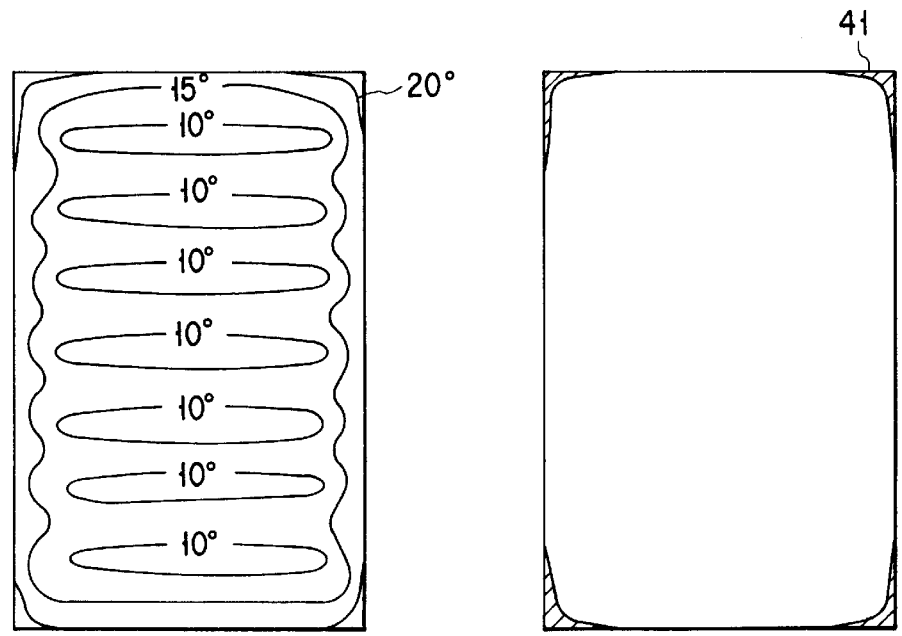
FIGS. 18A and 18B show in-plane contact angle distribution of a substrate, and a sketch of defect portions of the substrate, respectively, according to Experiment 1.

The surface free energy distribution-measuring apparatus of Example 2 was employed for the evaluation of a PVA (polyvinyl alcohol)-washing-out step in the line of manufacturing a liquid crystal display cell so as to investigate the correlation between the evaluation and the failure due to repelling by PI (polyimide). The target substrate employed and the measuring conditions were as follows.
(Target substrate)
 360 mm×460 mm, 0.7t, a color filter substrate (a two-plane substrate).
(Measuring conditions)
 Temperature of water: 20±0.5° C.
 Z-axis moving speed: 1.0 mm/s
 Z-axis spatial frequency: 3.6 mm
 Y-axis moving speed: 100 mm/s
 Z-axis spatial frequency: 3.6 mm
 Y-axis sampling number: 64 points/line
 Z-axis spatial frequency: 5.6 mm FIG. 18A illustrates the in-plane distribution of contact angle obtained in Experiment 1 wherein an advancing contact angle $\theta_a$ is employed. On the other hand, FIG. 18B is a sketch illustrating a state of PI-repelling on the substrate, exhibiting PI-repelling portions 41.

It is understood from FIGS. 18A and 18B that when the advancing contact angle $\theta_a$ is 20° or more, PI-repelling is caused. Namely, in order to avoid the PI-repelling, the advancing contact angle $\theta_a$ should be controlled to become less than 20°.

EXPERIMENT 2

Figure 19A:
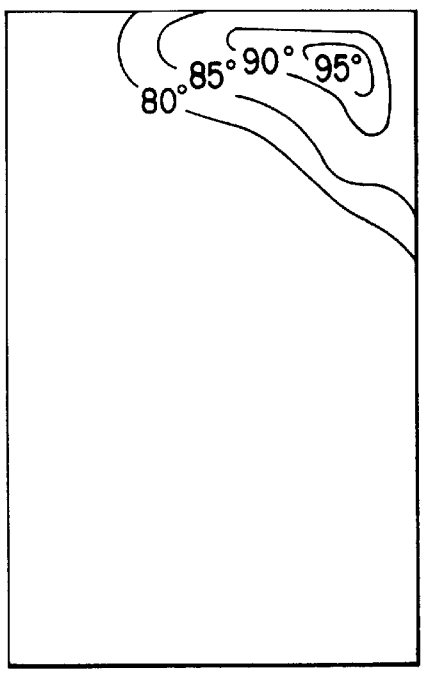
FIGS. 19A and 19B show in-plane contact angle distribution of a substrate, and in-plane pre-tilt angle distribution of the substrate for a liquid crystal display, respectively, according to Experiment 2.

The surface free energy distribution-measuring apparatus of Example 4 was employed for the evaluation of a PI (polyimide)-baking step in the line of manufacturing a liquid crystal display cell so as to investigate the correlation between the evaluation and the nonuniformity of pre-tilt angle after the assembling of liquid crystal cell. The pre-tilt angle means an angle between the longitudinal direction of liquid crystal cell and a substrate. The measurement of this pre-tilt angle was performed by making use of a pre-tilt angle-measuring apparatus using a laser microscope (Nippon Denshi Co.). The target substrate employed and the measuring conditions were as follows.
(Target substrate)
 360 mm×460 mm, 0.7t, a TFT substrate (a two-plane substrate).
(Measuring conditions)
 Sampling: 60 times/S
 Temperature of water: 20±0.5° C.
 Z-axis moving speed: 1.0 mm/s
 Z-axis spatial frequency: 0.017 mm
 Y-axis sampling number: 500 points/line
 Y-axis spatial frequency: 0.72 mm FIG. 19A illustrates the in-plane distribution of contact angle obtained in Experiment 2 wherein the in-plane distribution is indicated by an average angle $\theta_{av}$ of the advancing contact angle and receding contact angle, which is defined by the following equation. On the other hand, FIG. 19B shows an in-plane distribution of the pre-tilt angle.

$$\theta_{av} = \arccos\{(\cos\theta_r - \cos\theta_a)/2\}$$

Figure 19B:
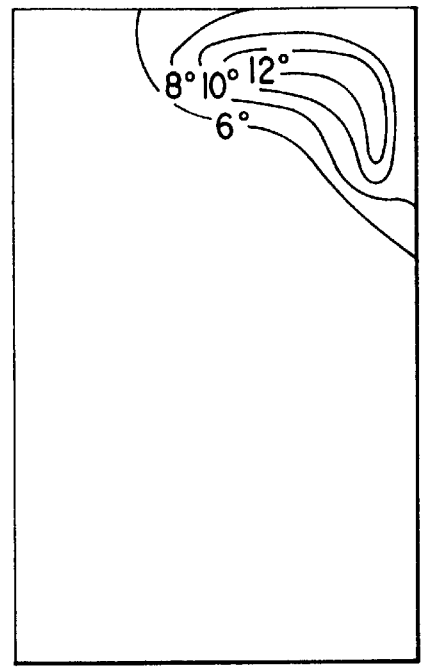

It is understood from FIGS. 19A and 19B that when the $\theta_{av}$ is 80° or more, a nonuniformity in pre-tilt angle is caused. Namely, in order to avoid a failure due to the nonuniformity in pre-tilt angle, the $\theta_{av}$ should be controlled to become less than 80°.

EXPERIMENT 3

The surface free energy distribution-measuring apparatus of Example 5 was employed for the evaluation of rubbing step in the line of manufacturing a liquid crystal display cell so as to investigate the correlation between the evaluation and the display failure after the assembling of liquid crystal cell. The target substrate employed and the measuring conditions were as follows.
(Target substrate)
 360 mm×460 mm, 0.7t, a color filter substrate (a two-plane substrate). The back surface thereof was washed with an organic solvent before measurement.
(Measuring conditions)
 Temperature of water: 20±0.5° C.
 Z-axis moving speed: 50 mm/s The measurement was performed in two directions, i.e. a direction parallel with the rubbing direction RD and a direction perpendicular to the rubbing direction RD (see FIGS. 22A and 22B).

Figure 21A:
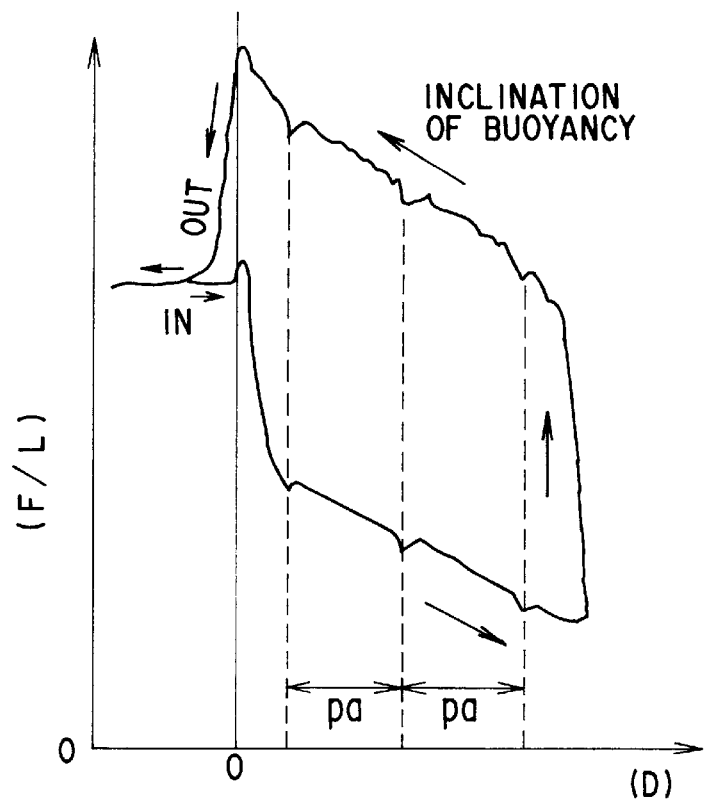
FIGS. 21A and 21B show correlation between immersing distance of a substrate and force worked thereon, according to Experiment 3.
Figure 21B:
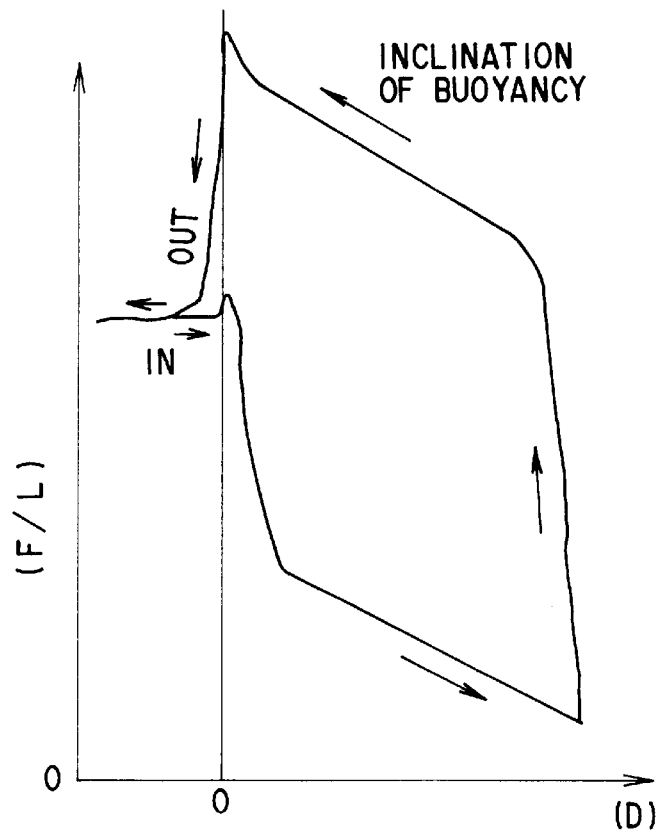

FIGS. 21A and 21B show the results wherein the force F worked on the substrate is divided by the circumferential length L of the substrate. In these graphs, the axis of abscissas indicates the immersing depth D of the substrate. When the substrate is moved parallel with the rubbing direction RD, a region which indicates a minimization of force worked on the substrate is periodically appeared at a cycle "pa". However, when the substrate is moved in perpendicular to the rubbing direction RD (FIG. 21B), such a region is not appeared at all.

Figure 20A:
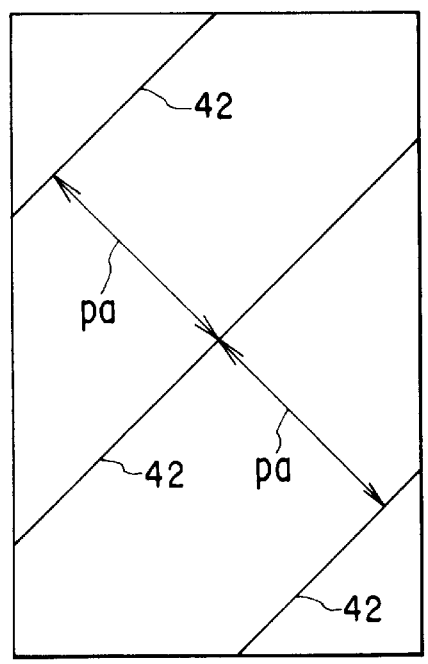
FIGS. 20A and 20B show in-plane contact angle distribution of a substrate, and a sketch of defect portions of the substrate for a liquid crystal display, respectively, according to Experiment 3.

Next, a buoyancy was measured from the inclination corresponding to the immersing depth D of the substrate as shown in FIGS. 21A and 21B, and then an average angle $\theta_{av}$ of the advancing contact angle and receding contact angle as defined by the following equation was made use of. These results, which are represented by an in-plane distribution, are shown in FIG. 20A.

$$\cos\theta_{av} = (\cos\theta_r - \cos\theta_a)/2$$

Figure 20B:
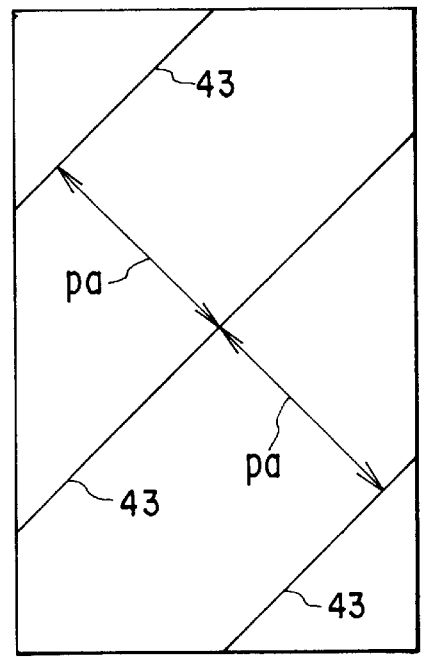

On the other hand, FIG. 20B shows a sketch illustrating a display failure after the assembling of liquid crystal cell. It is seen from FIG. 20B that the abnormal regions 42 of contact angle correspond to the display failure portions 43.

As explained above, when the surface free energy distribution-measuring apparatus according to this invention is employed, the controlling of the surface free energy, which is demanded of in view of obtaining desired properties of device, can be optimized step by step in a process of manufacturing a semiconductor device or a liquid crystal display, in particular in a process involving a large scaled substrate. Since a debug treatment can be performed at every manufacturing step, the cost for optimizing the process conditions can be reduced. Furthermore, when the surface free energy distribution-measuring apparatus according to this invention is employed in a sampling inspection or in a 100% inspection in the mass production, it is possible to assure a stabilized yield of product.

Additional advantages and modifications will readily occur to those skilled in the art. Therefore, the invention in its broader aspects is not limited to the specific details and representative embodiments, shown and described herein. Accordingly, various modifications may be made without departing from the spirit or scope of the general inventive concept as defined by the appended claims and their equivalents.

I claim:

1. An apparatus for measuring in-plane distribution of surface free energy, comprising:
   a trough containing a liquid for immersing a target substrate having a target surface, said liquid forming a liquid level;
   supporting means for supporting said target substrate so as to immerse said target substrate into said liquid in said trough such that said target surface intersects with said liquid level;
   measuring means for optically detecting a parameter, at plural locations in a horizontal direction, representing a state of meniscus to be formed at an intersection area of said target surface with a surface of said liquid, thereby obtaining one dimensional information consisting of measured values of said parameter at plural locations in a first direction of said target surface;
   moving means for relatively moving said liquid level and said target substrate in a vertical direction;
   said measuring means optically detecting said parameter in said first direction at plural locations in a second direction perpendicular to said first direction upon said moving means relatively moving said liquid level and said target substrate in said vertical direction, and accumulating said one dimensional information obtained at said different locations in said second direction to obtain two dimensional information consisting of measured values of said parameter all over said target surface; and
   distribution-forming means for forming an in-plane distribution on said target surface of said measured values of said parameter constituting said two dimensional information, or of conversion values calculated from said measured values of said parameter constituting said two dimensional information.

2. The apparatus according to claim 1, wherein each conversion value is a contact angle of said meniscus.

3. The apparatus according to claim 2, wherein said parameter is a height of said meniscus and said contact angle is calculated from the following equation:

$$\sin \theta = 1 - h^2(\rho_L - \rho_V)g/2\gamma_{LV}$$

wherein,
   $\theta$: said contact angle;
   h: said height of said meniscus;
   $\rho_V$: density of gas on said liquid;
   $\rho_L$: density of said liquid;
   g: acceleration of gravity;
   $\gamma_{LV}$: interfacial free energy between said gas and said liquid.

4. The apparatus according to claim 3, wherein said measuring means is provided with an optical detecting section extending along an entire width of said target surface in a horizontal direction so as to detect all of said parameter at a time along said entire width.

5. The apparatus according to claim 4, wherein said optical detecting section is provided with a plurality of optical sensor elements.

6. The apparatus according to claim 4, wherein said optical detecting section is provided with one end portion of a bundle of optical fibers connected to an optical sensor.

7. The apparatus according to claim 2, wherein said measuring means is provided with an optical detecting section movable in a horizontal direction along meniscus.

8. The apparatus according to claim 3, wherein said target substrate is transparent, and said measuring means is arranged to measure said parameter representing a state of said meniscus through a side of said target substrate which is opposite to said target surface.

9. The apparatus according to claim 2, wherein said parameter is a plurality set of two-dimensional coordinates (x, z) representing a curved surface of said meniscus, and said contact angle is calculated from the following equation:

$$\sin \theta = 1 - \{z(x)\}^2(\rho_L - \rho_V)g/2\gamma_{LV}$$

wherein,
   $\theta$: said contact angle;
   $\rho_V$: density of gas on said liquid;
   $\rho_L$: density of said liquid;
   g: acceleration of gravity;
   $\gamma_{LV}$: interfacial free energy between said gas and said liquid;
   x: horizontal distance from and perpendicular to said target surface; and
   z: vertical distance from said liquid level.

10. The apparatus according to claim 9, wherein said measuring means is provided with a light source and an optical detecting section, and said light source and said optical detecting section is integrally movable in a horizontal direction along meniscus.

11. The apparatus according to claim 1, wherein said trough is mounted on a vibration proof table.

12. The apparatus according to claim 1, wherein said trough is provided with means for controlling a temperature of said liquid.

13. The apparatus according to claim 1, wherein said trough is provided with means for removing soils on a surface of said liquid.

14. The apparatus according to claim 1, wherein said trough is provided with means for detecting surface free energy of said liquid.

15. A method of measuring in-plane distribution of surface free energy, comprising the steps of:
   immersing a target substrate having a target surface in a liquid;
   optically measuring a parameter at plural locations in a horizontal direction while keeping said target surface intersect with liquid level of said liquid, thereby obtaining one dimensional information consisting of measured values of said parameter at plural locations in a first direction on said target surface, said parameter representing a state of meniscus to be formed at an intersection area of said target surface with the surface of said liquid;
   relatively moving said liquid level and said target substrate in a vertical direction;
   continuing said optically measuring step during said step of relatively moving to accumulate said one dimensional information at plural locations in a second direction perpendicular to the first direction, thereby to obtain two dimensional information consisting of measured values of said parameter all over said target surface; and forming an in-plane distribution on said target surface of said measured values of said parameter constituting said two dimensional information, or of conversion values calculated from said measured values of said parameter constituting said two dimensional information.

16. The method according to claim 15, wherein each conversion value is a contact angle of said meniscus.

17. The method according to claim 16, wherein said parameter is a height of said meniscus and said contact angle is calculated from the following equation:

$$\sin \theta = 1 - h^2(\rho_L - \rho_V)g/2\gamma_{LV}$$

wherein,
 $\theta$: said contact angle;
 h: said height of said meniscus;
 $\rho_V$: density of gas on said liquid;
 $\rho_L$: density of said liquid;
 g: acceleration of gravity;
 $\gamma_{LV}$: interfacial free energy between said gas and said liquid.

18. The method according to claim 16, wherein said parameter is a plurality set of two-dimensional coordinates (x, z) representing a curved surface of said meniscus, and said contact angle is calculated from the following equation:

$$\sin \theta = 1 - \{z(x)\}^2(\rho_L - \rho_V)g/2\gamma_{LV}$$

wherein,
 $\theta$: said contact angle;
 $\rho_V$: density of gas on said liquid;
 $\rho_L$: density of said liquid;
 g: acceleration of gravity;
 $\gamma_{LV}$: interfacial free energy between said gas and said liquid;
 x: horizontal distance from and perpendicular to said target surface; and
 z: vertical distance from said liquid level.

* * * * *